(12) United States Patent
Friedrich et al.

(10) Patent No.: US 10,315,989 B2
(45) Date of Patent: Jun. 11, 2019

(54) FLUORINATED TENSIDES

(71) Applicant: MERCK PATENT GMBH, Darmstadt (DE)

(72) Inventors: Reiner Friedrich, Seeheim-Jugenheim (DE); Fanny Schooren, Ober-Ramstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 15/120,696

(22) PCT Filed: Feb. 18, 2015

(86) PCT No.: PCT/EP2015/000351
§ 371 (c)(1),
(2) Date: Aug. 22, 2016

(87) PCT Pub. No.: WO2015/124289
PCT Pub. Date: Aug. 27, 2015

(65) Prior Publication Data
US 2017/0008836 A1    Jan. 12, 2017

(30) Foreign Application Priority Data
Feb. 21, 2014    (EP) .................................... 14000617

(51) Int. Cl.
| C07C 309/17 | (2006.01) |
| C07C 49/167 | (2006.01) |
| C07C 19/08 | (2006.01) |
| C07C 43/04 | (2006.01) |

(52) U.S. Cl.
CPC ............ *C07C 309/17* (2013.01); *C07C 19/08* (2013.01); *C07C 43/04* (2013.01); *C07C 49/167* (2013.01)

(58) Field of Classification Search
None
See application file for complete search history.

(56) References Cited

U.S. PATENT DOCUMENTS

| 3,927,072 A | 12/1975 | Fox |
| 3,980,715 A | 9/1976 | Szur et al. |
| 4,049,668 A | 9/1977 | Szur et al. |
| 4,140,709 A | 2/1979 | Szur et al. |
| 4,968,599 A | 11/1990 | Pitt et al. |
| 4,988,610 A | 1/1991 | Pitt et al. |
| 5,162,405 A | 11/1992 | MacLeay |

(Continued)

FOREIGN PATENT DOCUMENTS

| CN | 102306833 A | 1/2012 |
| CN | 103333314 A | 10/2013 |

(Continued)

OTHER PUBLICATIONS

Office Action for Related European Patent Application No. 15 705 911.4 dated Jan. 31, 2018.

(Continued)

*Primary Examiner* — Medhanit W Bahta
(74) *Attorney, Agent, or Firm* — Millen White Zelano and Branigan, PC; John Sopp

(57) ABSTRACT

The present invention relates to novel compounds containing fluorinated end groups, to the use thereof as surface-active substances, and to compositions comprising these compounds.

17 Claims, 1 Drawing Sheet

(56) References Cited

U.S. PATENT DOCUMENTS

| | | |
|---|---|---|
| 6,706,923 B2 | 3/2004 | Haniff et al. |
| 6,800,788 B2 | 10/2004 | Bradley et al. |
| 6,809,216 B2 | 10/2004 | Bradley et al. |
| 6,890,608 B2 | 5/2005 | Morishima et al. |
| 7,635,789 B2 | 2/2009 | Thomas |
| 8,008,358 B2 | 8/2011 | Kirsch et al. |
| 8,263,800 B2 | 9/2012 | Murphy et al. |
| 9,115,062 B2 | 8/2015 | Hierse et al. |
| 2003/0092828 A1 | 5/2003 | Bradley et al. |
| 2003/0109626 A1 | 6/2003 | Bradley et al. |
| 2003/0153780 A1 | 8/2003 | Haniff et al. |
| 2004/0097761 A1 | 5/2004 | Erkey |
| 2007/0051916 A1 | 3/2007 | Flynn et al. |
| 2008/0093582 A1 | 4/2008 | Nagai et al. |
| 2008/0149878 A1 | 6/2008 | Kirsch et al. |
| 2009/0326083 A1 | 12/2009 | Flynn et al. |
| 2010/0003737 A1 | 1/2010 | Murphy et al. |
| 2011/0088594 A1 | 4/2011 | Claus et al. |
| 2012/0111233 A1 | 5/2012 | Hierse et al. |
| 2012/0184770 A1* | 7/2012 | Hintzer .......... C07C 51/27 562/540 |
| 2013/0269568 A1 | 10/2013 | Claus et al. |
| 2015/0246875 A1 | 9/2015 | Friedrich et al. |
| 2015/0337157 A1* | 11/2015 | Katsuhiko .......... C09D 127/16 |

FOREIGN PATENT DOCUMENTS

| | | |
|---|---|---|
| JP | 02-001765 A | 1/1990 |
| JP | H09111286 A | 4/1997 |
| JP | 2001133984 A | 5/2001 |
| JP | 2004018394 A | 1/2004 |
| JP | 2009-155289 A | 7/2009 |
| WO | 02103103 A2 | 12/2002 |
| WO | 03010128 A2 | 2/2003 |
| WO | 2006072401 A1 | 7/2006 |
| WO | 2009149807 A1 | 12/2009 |
| WO | 2010002623 A2 | 1/2010 |
| WO | 2010003567 A2 | 1/2010 |
| WO | 2010149262 A1 | 12/2010 |
| WO | 2011082770 A2 | 7/2011 |
| WO | 2012084118 A1 | 6/2012 |
| WO | 2014012661 A1 | 1/2014 |
| WO | WO-2014104416 A1 * | 7/2014 .......... C09D 127/16 |

OTHER PUBLICATIONS

International Search Report for PCT/EP2015/000351 dated Apr. 30, 2015.

Liu, Z. et al., "Water in carbon dioxide microemulsions with fluorinated analogues of AOT," Langmuir, Jan. 1, 2001, vol. 17, No. 2, pp. 274-277.

Pitt, A. R. et al., "The relationship between surfactant structure and limiting values of surface tension, in aqueous gelatin solution, with particular regard to multilayer coating," Colloids and Surfaces A: Physicochemical and Engineering Aspect, Aug. 1, 1996, vol. 114, pp. 321-335.

Liu, Z. et al., "Phase behaviors of aerosol-OT analogue fluorinated surfactants in 1,1,1,2-Tetrafluoroethane and Supercritical CO2," Ind. Eng. Chem. Res., 2007, vol. 46, pp. 22-28.

Kennedy, G. L. et al., "The Toxicology of Perfluorooctanoate," Critical Reviews in Toxicology, 2004, vol. 34, No. 4, pp. 351-384.

Il'In, A. A. et al, "Promising Prospects for Using Partially Fluorinated Alcohols as O-Nucleophilic Reagents in Organofluoric Synthesis," Organic Synthesis and Industrial Organic Chemistry, Zhurnal Prikladnoi Khimii, 2007, vol. 80, No. 3, pp. 405-420.

Pitt, A. R., "The efficiency of dynamic surface tension reductions within homologous series of surfactants in aqueous gelatin solution," Progr. Colloid Polym Sci, 1997, vol. 103, pp. 307-317.

English Abstract of WO2011082770, Publication Date: Jul. 14, 2011.

English Abstract of JP2004018394, Publication Date: Jan. 22, 2004.

English Abstract of JP2001133984, Publication Date: May 18, 2001.

English translation of Office Action for Related JP Patent Application No. 2016-553555 dated Oct. 15, 2018 (pp. 1-7).

Tatematsu et al: Journal of Oleo Science 1977, 26(6), 367-371.

* cited by examiner

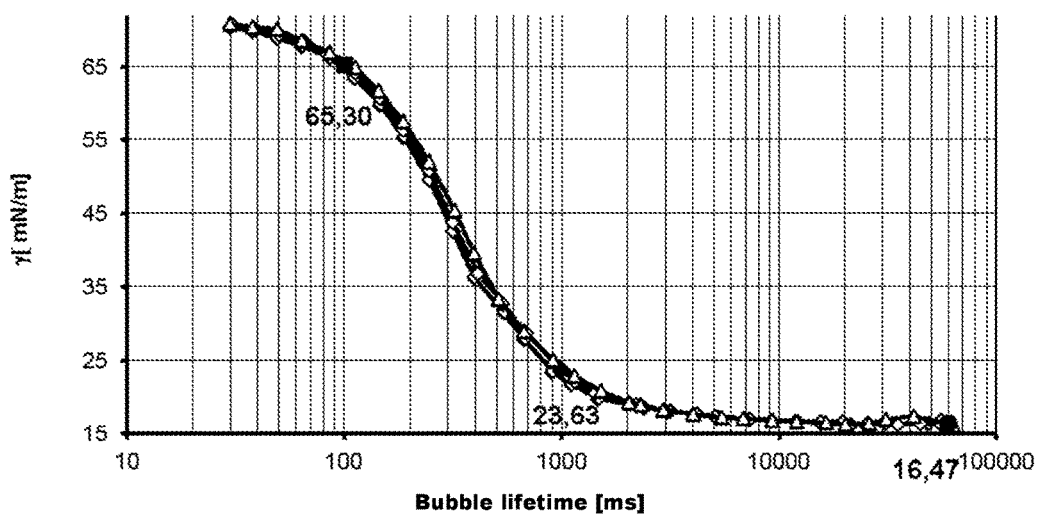

FLUORINATED TENSIDES

The present invention relates to novel compounds containing fluorinated end groups, to the use thereof as surface-active substances, and to compositions comprising these compounds.

Fluorine-containing surfactants have unique applicational properties owing to their special surface activity. Fluorosurfactants, whose static surface tension is very low (16-20 mN/m), can be employed in a very wide variety of applications and contribute, for example, to improved wetting of surfaces. Thus, they are used, for example, as interface promoters or emulsifiers or viscosity reducers in paints, coatings or adhesives.

Classical fluorosurfactants are built up from long-chain, perfluorinated alkyl chains (C6-C8) and are regarded as potentially bioaccumulative and toxic. In general, however, fluorosurfactants contain perfluoroalkyl substituents, which are broken down in the environment by biological and other oxidation processes to give perfluoroalkanecarboxylic acids and sulfonic acids. These are regarded as persistent and are in some cases suspected of causing health damage (G. L. Kennedy, Jr., J. L. Butenhoff, G. W. Olsen, J. C. O'Connor, A. M. Seacat, R. G. Perkins, L. B. Biegel, S. R. Murphy, D. G. Farrar, *Critical Reviews in Toxicology* 2004, 34, 351-384). In addition, longer-chain perfluoroalkanecarboxylic acids and sulfonic acids accumulate in the food chain. Shorter-chain fluorinated building blocks are more favourable with respect to their ecotoxicological profile, but often exhibit worse properties in their areas of application.

WO 03/010128 describes perfluoroalkyl-substituted amines, acids, amino acids and thioether acids which contain a $C_{3-20}$-perfluoroalkyl group. JP-A2001/133984 discloses surface-active compounds containing perfluoroalkoxy chains which are suitable for use in antireflection coatings. JP-A09/111286 discloses the use of perfluoropolyether surfactants in emulsions.

WO 2006/072401 and WO 2010/003567 describe surface-active compounds containing trifluoromethoxy groups. Compounds containing specific fluoroalkyl groups are described in U.S. Pat. No. 7,635,789, US 2008/0093582, JP 2004-18394 and WO 2010/002623. Partially fluorinated compounds are described in U.S. Pat. No. 7,737,307, EP 1 522 536 and WO 2010/002622.

Specific applications of sulfosuccinates and/or sulfotricarballylates containing various fluorinated side chains are described in U.S. Pat. Nos. 4,968,599 and 4,988,610 as well as U.S. Pat. No. 6,890,608 and in A. R. Pitt et al., Colloids and Surfaces A: Physicochemical and Engineering Aspects, 1996, 114, 321-335; A. R. Pitt, Progr. Colloid Polym. Sci, 1997, 103, 307-317 and Z.-T. Liu et al., Ind. Eng. Chem. Res. 2007, 46, 22-28. Further fluorosurfactants, in particular succinates and tricarballylates containing fluorinated alkyl groups, are described in WO 2009/149807, WO 2010/003567, WO 2010/149262, WO 2011/082770 and WO 2012/084118.

Furthermore, there is a demand for alternative surface-active substances which preferably do not break down on degradation to give long-chain persistent compounds.

Novel compounds have now been found which are suitable as surface-active substances and preferably do not have one or more of the abovementioned disadvantages.

The present invention relates firstly to compounds of the formula (I)

$$Z_n C_c D_d \text{spacer}_m X_x \quad (I)$$

where
$Z=R_f-O_{o1}-A^1_{a1}-O_{o2}-A^2_{a2}-O_{o3}-B_b-$
n=1, 2, 3, 4, 5 or 6, preferably 2-4, in particular 2-3,
$R_f$=fluorinated alkyl, linear or branched, preferably fluorinated $C_1$-$C_6$-alkyl, particularly preferably perfluorinated $C_1$-$C_4$-alkyl in particular perfluorinated $C_1$-$C_3$-alkyl,
$A^1$ and $A^2$=independently of one another —(CF$_2$)— or —(CF(CF$_3$)—CF$_2$)— or (CF$_2$—O)— or (CF$_2$—CF$_2$)—O—,
$a_1$ and $a_2$=independently of one another 0-4,
B=—CHF—CF$_2$—CR$^1$R$^2$—O—
b=1
$R^1$=H or alkyl, preferably $C_1$-$C_4$, in particular —CH$_3$ or —CH$_2$—CH$_3$
$R^2$=H or alkyl, preferably $C_1$-$C_4$, in particular —CH$_3$,
C=—CR'$_2$—CR"$_2$—O—,
c=0 or an integer from the range from 1 to 100,
R' and R"=independently of one another H or alkyl, in particular H or —CH$_3$ or —CH$_2$—CH$_3$
D=—CO—
d=0 or 1,
spacer=a saturated or unsaturated, branched or unbranched hydrocarbon unit, optionally containing heteroatoms,
m=0 or 1,
X is a hydrophilic group,
x=1, 2, 3 or 4, preferably 1,
o1, o2 and o3=independently of one another 0 or 1,
where all indices are selected so that no —O—O— bonds are present and the following compound is excluded:

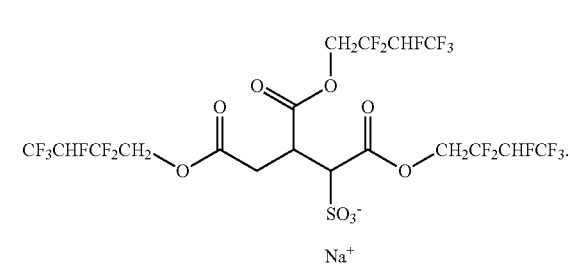

Compounds according to the invention preferably conform to the formula (I')

$$(ZC_cD_d)_n \text{spacer}_m X_x \quad (I)$$

where all variables have the meanings indicated for formula (I) and the said compound is excluded.

The hydrocarbon units of the spacer of the compounds of the formulae (I) and (I') can be aliphatic or aromatic units, optionally provided with heteroatoms. The group Z in the surface-active compounds here is preferably bonded to a saturated, branched or unbranched hydrocarbon unit, preferably to a saturated, branched or unbranched alkylene group, where one or more non-adjacent C atoms may be replaced by O or N, preferably O. In a variant of the invention, the preferred heteroatom-containing hydrocarbon unit used is a polyethylene or polypropylene glycol unit.

In a variant of the invention, the group Z occurs multiple times in the surface-active compound, preferably twice or three times. In another variant of the invention, the group Z occurs only once in the surface-active compound. In a variant of the invention, compounds of the formulae (I) and (I') may contain different group Z.

Preference is given to compounds of the formulae (I) and (I') in which n=2-3 and x=1.

In a variant of the invention, m is preferably 1.

Preference is given to compounds of the formulae (I) and (I') in which Z is equal to:

$R_f$—CHF—CF$_2$—CR$^1$R$^2$—O— or
$R_f$—O—CHF—CF$_2$—CR$^1$R$^2$—O— or
$R_f$—O—(CF$_2$)$_{1-4}$—CHF—CF$_2$—CR$^1$R$^2$—O— or
$R_f$—O—(CF$_2$)$_{1-4}$—O—CHF—CF$_2$—CR$^1$R$^2$—O— or
$R_f$—O—(CF(CF$_3$)—CF$_2$)$_{1-4}$—CHF—CF$_2$—CR$^1$R$^2$—O— or
$R_f$—O—(CF(CF$_3$)—CF$_2$)$_{1-4}$—O—CHF—CF$_2$—CR$^1$R$^2$—O— or
$R_f$—O—(CF$_2$—O)$_{1-4}$—CHF—CF$_2$—CR$^1$R$^2$—O— or
$R_f$—O—(CF$_2$—CF$_2$—O)$_{1-4}$—CHF—CF$_2$—CR$^1$R$^2$—O— or
$R_f$—O—(CF$_2$—O)$_{1-4}$—(CF$_2$—CF$_2$—O)$_{1-4}$—CHF—CF$_2$—CR$^1$R$^2$—O—.

Particular preference is given to compounds of the formulae (I) and (I') in which Z is equal to:
$R_f$—O—CHF—CF$_2$—CR$^1$R$^2$—O— or
$R_f$—O—(CF$_2$)$_{1-4}$—CHF—CF$_2$—CR$^1$R$^2$—O— or
$R_f$—O—(CF$_2$)$_{1-4}$—O—CHF—CF$_2$—CR$^1$R$^2$—O— or
$R_f$—O—(CF(CF$_3$)—CF$_2$)$_{1-4}$—CHF—CF$_2$—CR$^1$R$^2$—O— or
$R_f$—O—(CF(CF$_3$)—CF$_2$)$_{1-4}$—O—CHF—CF$_2$—CR$^1$R$^2$—O— or
$R_f$—O—(CF$_2$—O)$_{1-4}$—CHF—CF$_2$—CR$^1$R$^2$—O— or
$R_f$—O—(CF$_2$—CF$_2$—O)$_{1-4}$—CHF—CF$_2$—CR$^1$R$^2$—O— or
$R_f$—O—(CF$_2$—O)$_{1-4}$—(CF$_2$—CF$_2$—O)$_{1-4}$—CHF—CF$_2$—CR$^1$R$^2$—O—.

Z here is in particular=$R_f$—O—CHF—CF$_2$—CR$^1$R$^2$—O— or
$R_f$—O—(CF$_2$)$_{1-4}$—CHF—CF$_2$—CR$^1$R$^2$—O—, where $R^1$ and $R^2$ independently of one another=H, CH$_3$ or CH$_2$—CH$_3$. Preference is given here to compounds in which $R^1$ and $R^2$=H and those compounds in which $R^1$ or $R^2$=H.

Preference is given to compounds of the formulae (I) and (I')) in which Rf is equal to:
CF$_3$— or CF$_3$—CF$_2$— or CF$_3$—CF$_2$—CF$_2$—.

Especial preference is given to compounds of the formulae (I) and (I') in which n=2-3, x=1, Rf is equal to CF$_3$—, CF$_3$—CF$_2$— or CF$_3$—CF$_2$—CF$_2$— and Z is equal to:
$R_f$—O—CHF—CF$_2$—CR$^1$R$^2$—O— or
$R_f$—O—(CF$_2$)$_{1-4}$—CHF—CF$_2$—CR$^1$R$^2$—O— or
$R_f$—O—(CF$_2$)$_{1-4}$—O—CHF—CF$_2$—CR$^1$R$^2$—O— or
$R_f$—O—(CF(CF$_3$)—CF$_2$)$_{1-4}$—CHF—CF$_2$—CR$^1$R$^2$—O— or
$R_f$—O—(CF(CF$_3$)—CF$_2$)$_{1-4}$—O—CHF—CF$_2$—CR$^1$R$^2$—O— or
$R_f$—O—(CF$_2$—O)$_{1-4}$—CHF—CF$_2$—CR$^1$R$^2$—O— or
$R_f$—O—(CF$_2$—CF$_2$—O)$_{1-4}$—CHF—CF$_2$—CR$^1$R$^2$—O— or
$R_f$—O—(CF$_2$—O)$_{1-4}$—(CF$_2$—CF$_2$—O)$_{1-4}$—CHF—CF$_2$—CR$^1$R$^2$—O—.

Z is in particular=$R_f$—O—CHF—CF$_2$—CR$^1$R$^2$—O— or
$R_f$—O—(CF$_2$)$_{1-4}$—CHF—CF$_2$—CR$^1$R$^2$—O—, where $R^1$ and $R^2$ independently of one another=H, CH$_3$ or CH$_2$—CH$_3$. Preference is given here to compounds in which $R^1$ and $R^2$=H and those compounds in which $R^1$ or $R^2$=H.

Preference is given here to compounds in which the spacer is a saturated, branched or unbranched hydrocarbon unit and m=1.

Preferably, C=—CH$_2$—CHR"—O— or —CHR'—CH$_2$—O— where c=0 or an integer from the range from 1 to 100, preferably =1-100, and R' and R"=H or alkyl, in particular H or —CH$_3$ or —CH$_2$—CH$_3$.

Particular preference is given to compounds in which the said variables have the preferred meanings, in particular those in which all variables have the preferred meanings.

In the compounds according to the invention, X is a hydrophilic group, preferably an anionic, cationic, nonionic or amphoteric group.

A preferred anionic group X can be selected from —COO$^-$, —SO$_3^-$, —OSO$_3^-$, —PO$_3^{2-}$, —OPO$_3^{2-}$, —(OCH$_2$CH$_2$)$_s$—O—(CH$_2$)$_t$—COO$^-$, —(OCH$_2$CH$_2$)$_s$—O—(CH$_2$)$_t$—SO$_3^-$, —(OCH$_2$CH$_2$)$_s$—O—(CH$_2$)$_t$—OSO$_3^-$, —(OCH$_2$CH$_2$)$_s$—O—(CH$_2$)$_t$—PO$_3^{2-}$, —(OCH$_2$CH$_2$)$_s$—O—(CH$_2$)$_t$—OPO$_3^{2-}$ or from the formulae A to C,

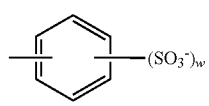

A

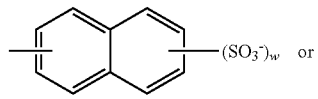

B

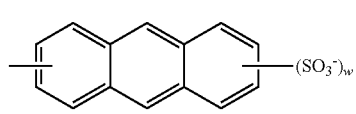

C where s stands for an integer from the range from 1 to 1,000, t stands for an integer selected from 1, 2, 3 or 4 and w stands for an integer selected from 1, 2 or 3.

The preferred anionic groups here include, in particular, —COO$^-$, —SO$_3^-$, —OSO$_3^-$, —PO$_3^{2-}$, —OPO$_3^{2-}$, the sub-formula A, and —(OCH$_2$CH$_2$)$_s$—O—(CH$_2$)$_t$—COO$^-$, —(OCH$_2$CH$_2$)$_s$—O—(CH$_2$)$_t$—SO$_3^-$ and —(OCH$_2$CH$_2$)$_s$—O—(CH$_2$)$_t$—OSO$_3^-$, where each one of these groups per se may be preferred.

The very particularly preferred anionic groups here include —SO$_3^-$, —OSO$_3^-$, —PO$_3^{2-}$, or OPO$_3^{2-}$. In particular, a sulfonate group —SO$_3^-$ is preferred.

Preferred counterion for anionic groups X is a monovalent cation, in particular H$^+$, an alkali-metal cation or NR$_4^+$, where R=H or C1-C6-alkyl and all R may be identical or different. Particular preference is given to Na$^+$, K$^+$, Li$^+$ and NH$_4^+$, particularly preferably Na$^+$.

A preferred cationic group X can be selected from

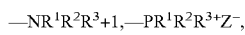

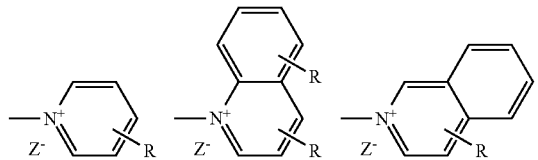

where R stands for H or C$_{1-4}$-alkyl in any desired position, Z$^-$ stands for Cl$^-$, Br$^-$, I$^-$, CH$_3$SO$_3^-$, CF$_3$SO$_3^-$, CH$_3$PhSO$_3^-$, PhSO$_3^-$ R$^1$, R$^2$ and R$^3$ each, independently of one another, stand for H, C$_{1-30}$-alkyl, Ar or CH$_2$Ar and Ar stands for an unsubstituted or mono- or polysubstituted aromatic ring or condensed ring systems having 6 to 18 C atoms, in which, in addition, one or two CH groups may be replaced by N.

The preferred cationic groups here include, in particular, —NR$^1$R$^2$R$^{3+}$Z$^-$ and

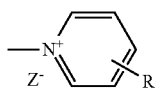

where each one of these groups per se may be preferred.

A preferred nonionic group can be selected from: linear or branched alkyl, where one or more non-adjacent C atoms have been replaced by O, S, and/or N,
—OH, —SH, —O-(glycoside)$_{o'}$, —S-(glycoside)$_{o'}$, —OCH$_2$—CHOH—CH$_2$—OH, —OCH$_2$Ar(—NCO)$_{p'}$, —OAr(—NCO)$_{p'}$, amine oxide,

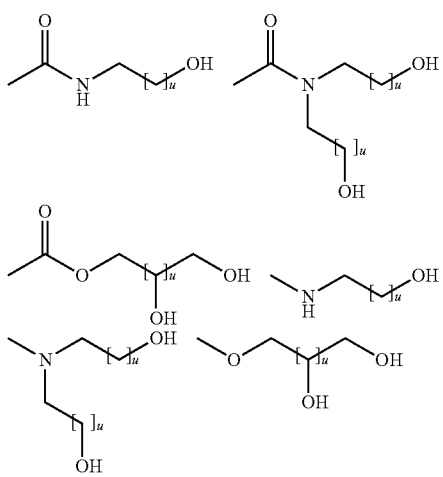

u stands for an integer from the range from 1 to 6, preferably 1 to 4
o' stands for an integer from the range from 1 to 10,
p' stands for 1 or 2,
Ar stands for an unsubstituted, mono- or polysubstituted aromatic ring or condensed ring systems having 6 to 18 C atoms, in which, in addition, one or two CH groups may be replaced by C=O and,
glycoside stands for an etherified carbohydrate, preferably for a mono- di-, tri- or oligoglucoside.

The preferred nonionic groups here include, in particular, linear or branched alkyl, where one or more non-adjacent C atoms have been replaced by O, S and/or N, —OH and —O-(glycoside)$_{d'}$.

If X=alkyl, where one or more non-adjacent C atoms have been replaced by O, S, and/or N, it is then preferably equal to R$^4$—(B-A)$_{m''}$— where R$^4$=H or C1-4-alkyl, in particular H or CH$_3$, A=linear or branched alkylene, preferably having 1 to 10 carbon atoms, in particular having 1 to 4 carbon atoms, B=O or S, preferably O, and m''=an integer preferably from the range from 1 to 100, particularly preferably 1 to 30.

The nonionic group X is particularly preferably the group R$^4$—(O—CH$_2$CHR$^5$)$_{m''}$— where m''=an integer from the range from 1 to 100, preferably 1 to 30, in particular 1-15, and R$^4$ and R$^5$=H or C1-4-alkyl, in particular H or CH$_3$. R$^4$—(B-A)$_{m''}$- is particularly preferably a polyethylene glycol or polypropylene glycol unit.

The nonionic group X is particularly preferably the group —CH(OH)—CH$_2$—NH—Sach where Sach=various sugars and the group Y—(CH$_2$—CH$_2$—O)$_v$—R$^4$ where Y=S, O or NH, preferably O, R$^4$=H or alkyl, preferably H or CH$_3$, and v=1-100, preferably 1-20, in particular 1-15.

A preferred amphoteric group can be selected from the functional groups of the acetyldiamines, the N-alkylamino acids, the N-alkylaminosulfonic acids, the betaines, the sulfobetaines, or corresponding derivatives, in particular selected from, where M stands for H or an alkali-metal ion, preferably Li$^+$, Na$^+$ or K$^+$:

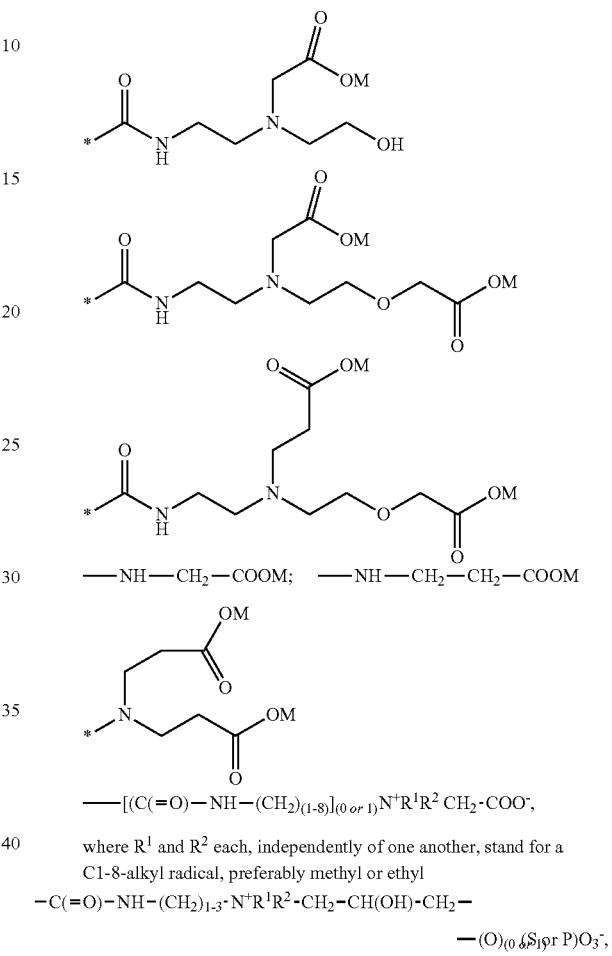

—NH—CH$_2$—COOM; —NH—CH$_2$—CH$_2$—COOM

—[(C(=O)—NH—(CH$_2$)$_{(1-8)}$]$_{(0\ or\ 1)}$N$^+$R$^1$R$^2$ CH$_2$-COO$^-$, where R$^1$ and R$^2$ each, independently of one another, stand for a C1-8-alkyl radical, preferably methyl or ethyl

—C(=O)—NH—(CH$_2$)$_{1-3}$-N$^+$R$^1$R$^2$-CH$_2$-CH(OH)-CH$_2$—

—(O)$_{(0\ or\ 1)}$P)O$_3^-$, where R$^1$ and R$^2$ each, independently of one another, stand for a C1-8-alkyl radical, preferably methyl or ethyl Particularly preferred compounds according to the invention are those which contain, as hydrophilic group X, one of the preferred anionic groups, the preferred nonionic groups or the preferred zwitterionic groups. Particular preference is given to compounds which contain the groups —SO$_3^-$, —OSO$_3^-$, —PO$_3^{2-}$ or OPO$_3^{2-}$, polyethylene glycols or polypropylene glycols, —CH(OH)—CH$_2$—NH—Sach, Y—(CH$_2$—CH$_2$—O)$_v$—R$^4$, betaines, or sulfobetaines. Preferred counterions here are Na$^+$, K$^+$ and NH$_4^+$, in particular Na$^+$. Particular preference is given to: —SO$_3^-$, polyethylene glycols or polypropylene glycols, sulfobetaines, the group —CH(OH)—CH$_2$—NH—Sach and the group Y—(CH$_2$—CH$_2$—O)$_v$—R$^4$. Sach here=various sugars and Y=S, O or NH, preferably O, R$^4$=H or alkyl, preferably H or CH$_3$, and v=1-100, preferably 1-20, in particular 1-15. Compounds where X=—SO$_3^-$ are particularly advantageous.

Compounds of the formulae (I) and (I') in which one or more of the variables have the preferred meanings are particularly advantageous. Compounds of the formulae (I)

and (I') in which all said variables have the preferred meanings are particularly advantageous.

Particular preference is given to compounds of the formulae (II) to (XI)
where Y=—(OCR"$_2$—CR'$_2$)0/1-Z
X=Na$^+$, K$^+$, Li$^+$, NH$^{4+}$, N(CH$_3$)$_4^{+}$,
Q=Cl, Br, I
R' and R"=independently of one another H or C$_1$-C$_4$ alkyl, preferably Y=—(OCH$_2$—CHR'$_2$)0/1-Z, where R'=H or C1-C2 alkyl,

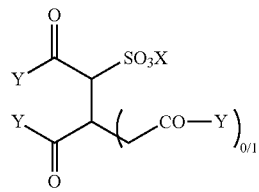

Formula (II)

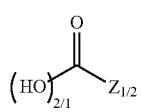

Formula (III)

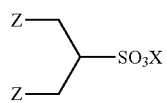

Formula (IV)

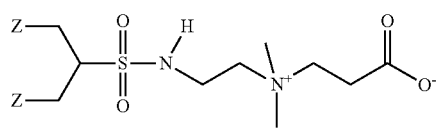

Formula (V)

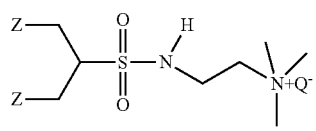

Formula (VI)

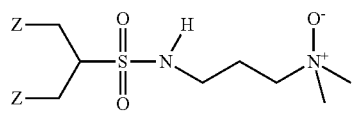

Formula (VII)

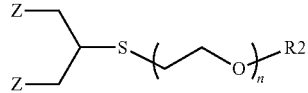

Formula (VIII)

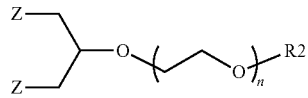

Formula (IX)

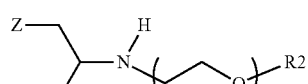

Formula (X)

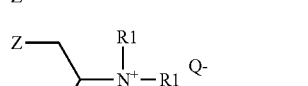

Formula (XI)

Particular preference is given to compounds of the formulae (II) to (XI) in which one or more of the variables have the preferred meanings. The variants of the formulae (II) to (XI) in which all variables have the preferred meanings, especially the particularly preferred meanings, are particularly preferred. Compounds of the formula (II) in which all said variables have the preferred meanings are particularly advantageous. The preferred hydrophilic groups indicated in the formulae (II) to (XI) may also have been replaced by other hydrophilic groups.

Particularly preferred compounds of the formulae (II) to (XI) are compounds in which Rf is equal to CF$_3$—, CF$_3$—CF$_2$— or CF$_3$—CF$_2$—CF$_2$— and Z is equal to:

R$_f$O—CHF—CF$_2$—CR$^1$R$^2$—O— or
R$_f$—O—(CF$_2$)$_{1-4}$—CHF—CF$_2$—CR$^1$R$^2$—O— or
R$_f$—O—(CF$_2$)$_{1-4}$—O—CHF—CF$_2$—CR$^1$R$^2$—O— or
R$_f$—O—(CF(CF$_3$)—CF$_2$)$_{1-4}$—CHF—CF$_2$—CR$^1$R$^2$—O— or
R$_f$—O—(CF(CF$_3$)—CF$_2$)$_{1-4}$—O—CHF—CF$_2$—CR$^1$R$^2$—O— or
R$_f$—O—(CF$_2$—O)$_{1-4}$—CHF—CF$_2$—CR$^1$R$^2$—O— or
R$_f$—O—(CF$_2$—CF$_2$—O)$_{1-4}$—CHF—CF$_2$—CR$^1$R$^2$—O— or
R$_f$—O—(CF$_2$—O)$_{1-4}$—(CF$_2$—CF$_2$—O)$_{1-4}$—CHF—CF$_2$—CR$^1$R$^2$—O—.

Z here is in particular=R$_f$O—CHF—CF$_2$—CR$^1$R$^2$—O— or R$_f$—O—(CF$_2$)$_{1-4}$—CHF—CF$_2$—CR$^1$R$^2$—O—, where R$^1$ and R$^2$ independently of one another=H, —CH$_3$ or —CH$_2$—CH$_3$. Preference is given here to compounds in which R$^1$ and R$^2$=H and those compounds in which R$^1$ or R$^2$=H.

Preference is given here to compounds which contain, as X, the groups —SO$_3^-$, —OSO$_3^-$, —PO$_3^{2-}$ or OPO$_3^{2-}$, polyethylene glycols or polypropylene glycols, —CH(OH)—CH$_2$—NH—Sach, Y—(CH$_2$—CH$_2$—O)$_v$—R$^4$, betaines, or sulfobetaines. Preferred counterions here are Na$^+$, K$^+$ and NH$_4^+$, in particular Na$^+$. Particular preference is given to: —SO$_3^-$, polyethylene glycols or polypropylene glycols, sulfobetaines, the group —CH(OH)—CH$_2$—NH—Sach and the group Y—(CH$_2$—CH$_2$—O)$_v$—R$^4$. Sach here=various sugars and Y=S, O or NH, preferably O, R$^4$=H or alkyl, preferably H or CH$_3$, and v=1-100, preferably 1-20, in particular 1-15. Compounds where X=—SO$_3^-$ are particularly advantageous.

Especial preference is given to compounds of the formula (II) and also compounds of the formulae (II-a) (II-b), (II-c) and (II-d), in which the variables have the meanings indicated for the formulae (I), (I') or (II), in particular the preferred meanings.

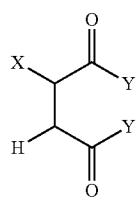

(II-a)

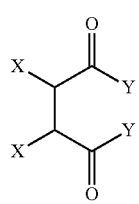

(II-b)

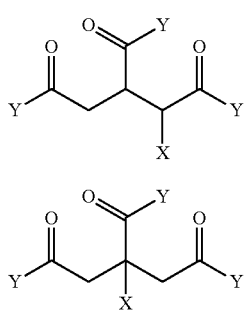

(II-c)

(II-d)

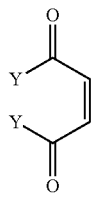

(XIII)

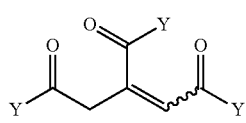

(XIV)

Examples of particularly advantageous compounds are succinates and tricarballylates in which Y, Z and X have the meaning described above, in particular the preferred meanings.

Particularly preferred compounds of the formulae (II) and (IIa) to (IId) are compounds in which Rf is equal to $CF_3$—, $CF_3$—$CF_2$— or $CF_3$—$CF_2$—$CF_2$— and Z is equal to:
$R_fO$—CHF—$CF_2$—$CR^1R^2$—O— or
$R_f$—O—$(CF_2)_{1-4}$—CHF—$CF_2$—$CR^1R^2$—O— or
$R_f$—O—$(CF_2)_{1-4}$—O—CHF—$CF_2$—$CR^1R^2$—O— or
$R_f$—O—$(CF(CF_3)$—$CF_2)_{1-4}$—CHF—$CF_2$—$CR^1R^2$—O— or
$R_f$—O—$(CF(CF_3)$—$CF_2)_{1-4}$—O—CHF—$CF_2$—$CR^1R^2$—O— or
$R_f$—O—$(CF_2$—O$)_{1-4}$—CHF—$CF_2$—$CR^1R^2$—O— or
$R_f$—O—$(CF_2$—$CF_2$—O$)_{1-4}$—CHF—$CF_2$—$CR^1R^2$—O— or
$R_f$—O—$(CF_2$—O$)_{1-4}$—$(CF_2$—$CF_2$—O$)_{1-4}$—CHF—$CF_2$—$CR^1R^2$—O—.

Z here is in particular=$R_fO$—CHF—$CF_2$—$CR^1R^2$—O— or $R_f$—O—$(CF_2)_{1-4}$—CHF—$CF_2$—$CR^1R^2$—O—, where $R^1$ and $R^2$ independently of one another=H, —$CH_3$ or —$CH_2$—$CH_3$. Preference is given here to compounds in which $R^1$ and $R^2$=H and those compounds in which $R^1$ or $R^2$=H.

Preference is given here to compounds which contain, as X, the groups —$SO_3^-$, —$OSO_3^-$, —$PO_3^{2-}$ or $OPO_3^{2-}$, polyethylene glycols or polypropylene glycols, —CH(OH)—$CH_2$—NH—Sach, Y—$(CH_2$—$CH_2$—O$)_v$—$R^4$, betaines, or sulfobetaines. Preferred counterions here are $Na^+$, $K^+$ and $NH_4^+$, in particular $Na^+$. Particular preference is given to: —$SO_3^-$, polyethylene glycols or polypropylene glycols, sulfobetaines, the group —CH(OH)—$CH_2$—NH—Sach and the group —Y—$(CH_2$—$CH_2$—O$)_v$—$R^4$. Sach here=various sugars and Y=S, O or NH, preferably O, $R^4$=H or alkyl, preferably H or $CH_3$, and v=1-100, preferably 1-20, in particular 1-15. Compounds where X=—$SO_3^-$ are particularly advantageous.

The compounds according to the invention can be prepared by processes known to the person skilled in the art.

The compounds of the formula (II) according to the invention can preferably be prepared by esterification of maleic acid and aconitic acid or anhydrides or acid chlorides thereof using one or more alcohols of the formula (XII), where Y has the meanings described above, in particular the preferred meanings

Y—H (XII)

and subsequent addition onto the double bond in order to introduce the group X.

The invention thus furthermore relates to the corresponding maleic acid and aconitic acid esters of the formulae (XIII) and (XIV) respectively:

The variables in the formulae (XIII) and (XIV) have the meanings described above, in particular also the preferred meanings. The formula (XIV) shows the presence of Z/E double-bond isomers.

The compounds according to the invention can also preferably be prepared by esterification of hydroxysuccinic acid and citric acid using one or more alcohols of the formula (XII) and subsequent functionalisation of the hydroxyl groups in order to introduce the group X.

The alcohols used are commercially available and/or their preparation starting from commercially available starting materials is familiar to the person skilled in the art or they can be prepared analogously to known synthetic processes, for example free-radical addition, see: A. A. Il'in et al., Russian Journal of Applied Chemistry, 2007, Vol. 80, No. 3, pp. 405-418.

The synthesis of succinates or tricarballylates according to the invention is preferably carried out as described in WO 2014/012661 in a two-step synthesis via the corresponding maleates or hydroxysuccinates or the corresponding aconitic or citric acid esters. The preparation of further compounds of the formula (II) according to the invention can be carried out analogously to the illustrative reactions shown above. The preparation of further compounds of the formula (II) according to the invention can also be carried out by other methods known per se to the person skilled in the art from the literature. In particular, other esterification catalysts can be used. These said syntheses are described in WO 2010/149262, WO 2011/082770 and WO 2012/084118. The disclosures in the cited references hereby expressly also belong to the disclosure content of the present application. The preparation of further compounds according to the invention can be carried out analogously to the illustrative reactions shown above or can be carried out by other methods known per se to the person skilled in the art from the literature.

Advantages of the compounds according to the invention, preferably of the formula (II), in particular of the formulae (IIa) to (IId), may be, in particular:
  a surface activity which is equal or superior to that of conventional hydrocarbon surfactants with respect to efficiency and/or effectiveness,
  biological and/or abiotic degradability of the substances without the formation of persistent perfluorinated degradation products, such as PFOA (perfluorooctanoic acid) or PFOS (perfluorooctanesulfonate),
  can be prepared by simple processes,
  weak foaming action and/or low foam stabilisation,
  good processability in formulations and/or
  storage stability.

The compounds according to the invention can preferably have a particular surface activity. The compounds of the formula (I) according to the invention, in particular the compounds of the formula (II), preferably of the formulae (II-a), (II-b), (II-c) and (II-d), may have significantly improved environmental properties compared with the fluorosurfactants of the prior art, since they do not degrade chemically or biologically to give long-chain PFCAs or PFASs.

The compounds according to the invention can preferably be converted completely into mineralisable/regeneratable compounds by corresponding environmental influences.

The degradation of the compounds according to the invention can preferably take place by two mechanisms. In the first step, the carbon skeleton can be degraded by biological activity to the extent that (partially) fluorinated compounds form, which are non-toxic and have a high vapour pressure (b.p.<140° C.). Owing to the high volatility, these compounds are able to reach the atmosphere and can be decomposed in the stratosphere by the intense UV radiation prevailing therein to give low-molecular-weight compounds (HF, $COF_2$ etc.). These decomposition products can then be washed out of the atmosphere with rain, transferred into the ground and mineralised therein.

In order to be able to pass through this cycle, it is preferred that the end products are not perfluorinated in the biological decomposition and (stable) salts cannot form.

The alkyl substitution on the a carbon can preferably result in these secondary or tertiary alcohols not being oxidised as a priority during biological degradation to give low-volatility compounds, such as, for example, carboxylic acids.

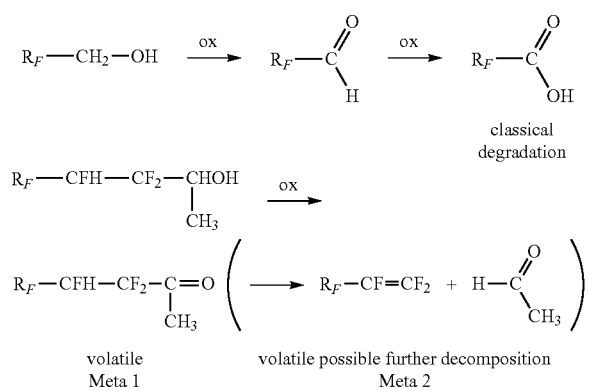

classical degradation volatile Meta 1 volatile possible further decomposition Meta 2

The unfluorinated part of the compounds according to the invention is readily degradable via biological mechanisms. In all cases, the molecules Meta 1 or Meta 2 remain as biologically unconvertable radicals which have a sufficiently high vapour pressure in order to be able to enter the atmosphere from the water or soil. According to literature data, Meta 2 is decomposed within a short time in the stratosphere by UV radiation (see "Atmospheric Fate of various fluorocarbons, Master Thesis Yi Tang, Massachusetts Institute of Technology, 1993).

The invention furthermore relates to a process for the degradation of fluorine-containing compounds comprising the following steps:
a) biological and/or abiotic degradation of the carbon skeleton of the fluorine-containing compounds with formation of, preferably non-toxic, fluorine-containing compounds having a sufficiently high vapour pressure,
b) conversion of the fluorine-containing compounds having a high vapour pressure formed in step a) into a gas phase,
c) degradation of the fluorine-containing compounds having a high vapour pressure formed in step a) to give low-molecular-weight compounds by UV irradiation in the gas phase,
d) conversion of the low-molecular-weight compounds formed in step c) from the gas phase into a liquid and/or solid phase,
e) mineralisation of the low-molecular-weight compounds of the liquid and/or solid phase formed step c).

Preferably, no fluorine-containing, salts are formed in step a). In particular, no perfluorinated compounds are formed in step a).

Fluorine-containing surfactants are preferably subjected to the degradation process described, in particular surfactants which are based on partially fluorinated and/or α-alkylated alcohols.

In the said degradation process, compounds of the formula (I), in particular those of the formula (II), preferably those of the formulae (II-a), (II-b), (II-c) and (II-d), are preferably employed.

In the degradation process, compounds of the formula (XV) and/or of the formula (XVI) can preferably be formed in step a):

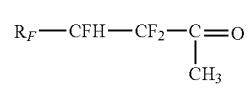

Formula (XV)

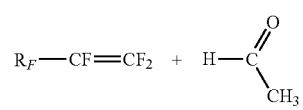

Formula (XVI)

The present invention secondly relates to the use of the compounds according to the invention and the preferred embodiments described above as surface-active agents, for example for improving the flow behaviour and the wetting capacity of coating formulations. Fluorosurfactants of the formulae (II) to (XI) are preferably used, in particular the said particularly preferred compounds, preferably compounds of the formulae (II-a), (II-b), (II-c) and (II-d).

Besides the compounds of the formula (I), preferably of the formula (II), in particular of the formulae (II-a), (II-b), (II-c) and (II-d), the mixtures according to the invention may also comprise solvents, additives, assistants and fillers as well as non-fluorinated surfactants. Mention may be made by way of example of silicone particles, plasticisers and surface-modified pigments.

Preferred areas of use are, for example, the use of the fluorosurfactants according to the invention, preferably those of the formula (II), in particular of the formulae (II-a), (II-b), (II-c) and (II-d), as additives in preparations for surface coating, such as paints, coatings, protective coatings, special coatings in electronic or semiconductor applications (for example photoresists, top antireflective coatings, bottom antireflective coatings) or in optical applications (for example photographic coatings, coatings of optical elements), in agrochemicals, in polishes and waxes, for example for furniture, flooring and automobiles, in particular in floor polishes, in fire-extinguishing compositions, lubricants, in photolithographic processes, in particular in immersion photolithography processes, for example in developer solutions, rinse solutions, immersion oils and/or in the photoresists themselves, especially for the production of printed circuits or in additive preparations for addition to corresponding preparations.

In addition, the compounds which can be used in accordance with the invention as surfactant are suitable for washing and cleaning applications, and for use as additives/surfactants in cosmetic products, such as, for example, hair- and body-care products (for example shampoos, hair rinses and hair conditioners), foam baths, creams or lotions having one or more of the following functions: emulsifiers, wetting agents, foaming agents, glidants, antistatic, agents for increasing the resistance to skin greases.

For use, the fluorosurfactants according to the invention are usually introduced into correspondingly designed preparations. Usual use concentrations are 0.01-1.0% by weight of the surfactants according to the invention, based on the preparation as a whole. The present invention likewise relates to corresponding compositions comprising the fluorosurfactants according to the invention. Such compositions preferably comprise a vehicle which is suitable for the respective application, and optionally further active substances and/or optionally assistants. Preferred compositions are paint and coating preparations, fire-extinguishing compositions, lubricants, washing and cleaning compositions and de-icers or developer solutions, rinse solutions, immersion oils and photoresists for photolithographic processes, in particular for immersion photolithography processes and in particular for the production of printed circuits, agrochemicals, floor polishes, cosmetic products, cosmetic products or hydrophobicising compositions for textile finishing or glass treatment. Preferred compositions here are paint and coating preparations and printing inks.

In addition, the present invention also relates to water-based coating formulations which comprise the fluorosurfactants according to the invention, alone or in a mixture with additives. Coating formulations based on the following synthetic film formers are preferably used: polycondensation resins, such as alkyd resins, saturated/unsaturated polyesters, polyamides/imides, silicone resins; phenolic resins; urea resins and melamine resins, polyaddition resins, such as polyurethanes and epoxy resins, polymerisation resins, such as polyolefins, polyvinyl compounds and polyacrylates.

In addition, the fluorosurfactants according to the invention are also suitable for use in coatings based on natural products and modified natural products. Preference is given to coatings based on oils, polysaccharides, such as starch and cellulose, and also based on natural resins, such as cyclic oligoterpenes, polyterpenes and/or shellac.

The fluorosurfactants according to the invention can be used both in physically curing (thermoplastics) and also in crosslinking (elastomers and thermosets) aqueous coating systems. The fluorosurfactants according to the invention preferably improve the flow and wetting properties of the coating systems.

The present invention relates to all uses mentioned here of fluorosurfactants to be employed in accordance with the invention. The respective use of fluorosurfactants for the said purposes is known to the person skilled in the art, meaning that the use of the fluorosurfactants to be employed in accordance with the invention presents no problems.

The complete disclosure content of all applications and publications cited is incorporated into this application by way of reference. For the present invention, both the plural form of a term and also the singular form of a term also means the respective other form, unless expressly indicated otherwise. All features of the present invention can be combined with one another in any way, unless certain features are mutually exclusive. This applies, in particular, to preferred and particularly preferred features. Further features, advantages and variants of the invention also arise from the claims and examples. The following examples explain the present invention in greater detail without restricting the scope of protection.

EXAMPLES

Abbreviations

MTBE tert-butyl methyl ether
b.p. boiling point
DM demineralised

Example 1

2-Sulfosuccinic acid bis-[2-(2,2,3-trifluoro-3-heptafluoropropyloxypropoxy)ethyl] ester sodium

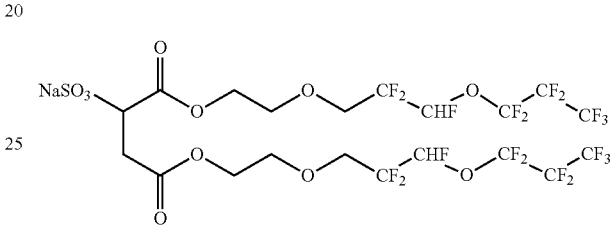

20.20 g of 2,2,3-trifluoro-3-heptafluoropropyloxypropan-1-ol, 6.56 g of ethylene carbonate and 0.95 g of potassium carbonate are reacted at 130° C. for 75 hours. 50 ml of semi-concentrated HCl are added to the reaction mixture, which is extracted by shaking with 3×25 ml of MTBE, the combined organic phases are dried over sodium sulfate, and the solvent is distilled off. Crude yield: 21.75 g Distillative work-up gives 12.9 g of 96% product (b.p. 78° C./10 mbar). GC-MS and NMR investigations confirm the structure 12.65 g of the alcohol, 1.72 g of maleic anhydride and 0.3 g of p-toluenesulfonic acid (catalyst) in 60 ml of toluene are boiled under reflux for 96 hours. The water liberated during the reaction is removed with the aid of the water separator. 30 ml of DM water are added to the reaction mixture, and the phases are separated. The aqueous phase is subsequently extracted with 3×25 ml of MTBE, the combined organic phases are washed with 1×30 ml of water and with 1×30 ml of sat. NaCl solution and dried over sodium sulfate, filtered off, and the solvent is distilled off.

Distillation in a high vacuum gives 8.22 g of the corresponding ester in 96% purity (b.p. 180°/6.7*10$^{-2}$ mbar).

6.6 g of diester are dissolved in 12 ml of 2-propanol, and 5.57 g of 39% aqueous sodium hydrogensulfite solution are added at 50° C. The pH is adjusted to 5-6 using 32% sodium hydroxide solution and stirred at 100° C. for 41 h.

40 ml of DM water are added to the reaction mixture, and the phases are separated.

The aqueous phase is subsequently extracted with 3×25 ml of MTBE, the combined organic phases are washed with 1×30 ml of water and 1×30 ml of saturated NaCl solution and dried over sodium sulfate.

Removal of the solvent by distillation gives a yield of 3.90 g,

The static surface tension $\gamma_{stat.}$ is determined by the method indicated and is 17.69 mN/m for a solution comprising 0.1% by weight of the compound and 16.78 mN/m for a solution comprising 1% by weight of the compound.

The dynamic surface tension is shown in the FIG. 4.

Example 2: Determination of the Static Surface Tension

The static surface tensions γ of aqueous surfactant solutions having various concentrations c (grams per liter) are determined.

Instrument: Dataphysics tensiometer (model DCAT 11)
Temperature of the measurement solutions: 20°±0.2° C.
Measurement method employed: measurement of the surface tension using the Wilhelmy plate method in accordance with DIN EN 14370.
Plate: platinum, length=19.9 mm In the plate method, the surface or interfacial tension of the surfactant solution is calculated from the force acting on the wetted length of a plate, in accordance with the following formula.

$$\gamma = \frac{F}{L \cdot \cos\theta} = \frac{F}{L}$$

γ=interfacial or surface tension; F=force acting on the balance; L=wetted length (19.9 mm); θ=contact angle. The plate consists of roughened platinum and is thus optimally wetted so that the contact angle θ is close to 0°. The term cos θ therefore approximately reaches the value 1, so that only the measured force and the length of the plate have to be taken into account.

Example 3: Determination of the Dynamic Surface Tension

The dynamic surface tension γ of a 0.1% (percent by weight) aqueous solution of the compound to be investigated is determined.

Measurement method employed: measurement of the surface tension using the bubble pressure method
Instrument: SITA tensiometer (model t 60)
Temperature of the measurement solutions: 20° C.±0.2° C.

During measurement of the dynamic surface tension, air bubbles are forced at different speeds through a capillary into the surfactant solution. The surface tension can be determined from the resultant pressure change as a function of the bubble lifetime using the following equation:

$$\gamma = \frac{r(p_{max} - \rho \cdot g \cdot h)}{2}$$

$p_{max}$=maximum pressure, ρ=density of the liquid, h=immersion depth, r=radius of the capillary

BRIEF DESCRIPTION OF THE FIGURES

FIG. 1: dynamic surface tensions γ of the surfactant from Example 1

The invention claimed is:
1. A compound of the formula (I')

$$(ZC_cD_d)_n\text{spacer}_mX_x \qquad (I')$$

wherein
Z=$R_f$—O—CHF—CF$_2$—CR$^1$R$^2$—O— or
$R_f$—O—(CF$_2$)$_{1-4}$—CHF—CF$_2$—CR$^1$R$^2$—O— or
$R_f$—O—(CF$_2$)$_{1-4}$—O—CHF—CF$_2$—CR$^1$R$^2$—O— or
$R_f$—O—(CF(CF$_3$)—CF$_2$)$_{1-4}$—CHF—CF$_2$—CR$^1$R$^2$—O— or
$R_f$—O—(CF(CF$_3$)—CF$_2$)$_{1-4}$—O—CHF—CF$_2$—CR$^1$R$^2$—O— or
$R_f$—O—(CF$_2$—O)$_{1-4}$—CHF—CF$_2$—CR$^1$R$^2$—O— or
$R_f$—O—(CF$_2$—CF$_2$—O)$_{1-4}$—CHF—CF$_2$—CR$^1$R$^2$—O— or
$R_f$—O—(CF$_2$—O)$_{1-4}$—(CF$_2$—CF$_2$—O)$_{1-4}$—CHF—CF$_2$—CR$^1$R$^2$—O—, n'=1, 2, 3, 4, 5 or 6,
$R_f$=fluorinated alkyl, linear or branched,
R$^1$=H or alkyl,
R$^2$=H or alkyl,
C=—CR'$_2$—CR"$_2$—O—,
c=0 or an integer from the range from 1 to 100,
R' and R"=independently of one another H or alkyl,
D=—CO—
d=0 or 1,
provided that at least one of c or d is not 0
spacer=a saturated or unsaturated, branched or unbranched hydrocarbon unit, optionally containing heteroatoms,
m=0 or 1,
X is a hydrophilic anionic, cationic, non-ionic or amphoteric group,
x=1, 2, 3 or 4.

2. A compound according to claim 1, wherein n' is equal to 2-3.
3. A compound according to claim 1, wherein $R_f$=fluorinated C1-C6-alkyl.
4. A compound according to claim 1, wherein x=1.
5. A compound according to claim 1, wherein Z is equal to:
$R_f$—O—CHF—CF$_2$—CR$^1$R$^2$—O— or
$R_f$—O—(CF$_2$)$_{1-4}$—CHF—CF$_2$—CR$^1$R$^2$—O—
wherein R$^1$ and R$^2$ independently of one another =H, —CH$_3$ or —CH$_2$—CH$_3$.
6. A compound of claim 1, wherein Rf=CF$_3$— or CF$_3$—CF$_2$— or CF$_3$—CF$_2$—CF$_2$—.
7. A compound according to claim 1, wherein the compound is of one of the formulae (II) to (XI) where:
Z is as defined in claim 1,
Y=Z optionally bonded through a —OCR"$_2$—CR'$_2$— group,
X'=Na$^+$, K$^+$, Li$^+$, NH$_4^+$, or N(CH$_3$)$_4^+$,
Q=Cl, Br, or I and
R' and R"=independently of one another H or C1-C4 alkyl

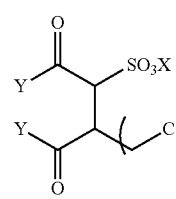

Formula (II)

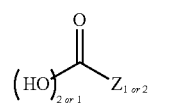

Formula (III)

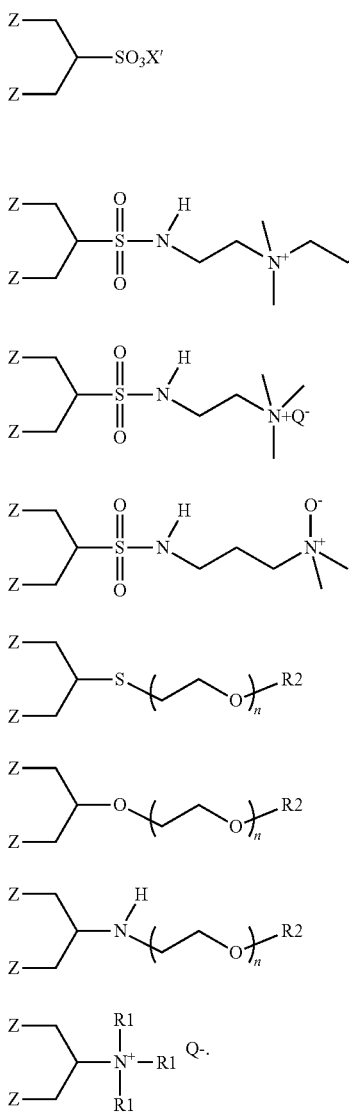

Formula (IV)

Formula (V)

Formula (VI)

Formula (VII)

Formula (VIII)

Formula (IX)

Formula (X)

Formula (XI)

8. A compound according to claim 7, which is of one of the formulae (II-a), (II-b), (II-c) or (II-d):

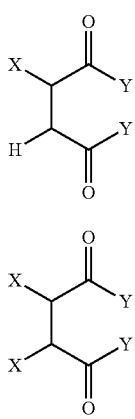

(II-a)

(II-b)

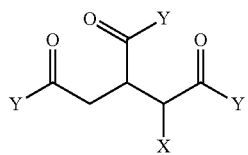

(II-c)

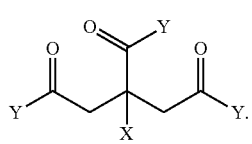

(II-d)

9. A compound of claim 7, characterised in that Y=Z optionally bonded through a —OCH$_2$—CHR'$_2$ group, wherein R'=H or C1-C2 alkyl.

10. A compound of claim 1, wherein Rf=CF$_3$-, CF$_3$—CF$_2$— or CF$_3$—CF$_2$—CF$_2$—, Z=R$_f$—O—CHF—CF$_2$—CR$^1$R$^2$—O— or R$_f$—O—(CF$_2$)$_{1-4}$—CHF—CF$_2$—CR$^1$R$^2$—O—, wherein R$^1$ and R$^2$ independently of one another =H, —CH$_3$ or —CH$_2$—CH$_3$ and X is one of the groups —SO$_3^-$, —OSO$_3^-$, —PO$_3^{2-}$ or OPO$_3^{2-}$, polyethylene glycol or polypropylene glycol, —CH(OH)—CH$_2$—NH—Sach wherein Sach=a sugar, Y—(CH$_2$—CH$_2$—O)$_v$—R$^4$ wherein Y in this formula=S, O or NH, R$^4$=H or alkyl and v=1-100, betaine or sulfobetaine.

11. A compound of claim 1, wherein R$^1$=C1-C4 alkyl and R$^2$=C1-C4 alkyl.

12. A compound of claim 1, wherein R$^1$=CH$_3$ or —CH$_2$—CH$_3$ and R$^2$=—CH$_3$.

13. A compound according to claim 1, wherein R$_f$=fluorinated C1-C3-alkyl.

14. A compound according to claim 1, wherein X is selected from the group consisting of anionic, cationic, nonionic and amphoteric groups:

wherein the anionic groups have one of the following anions with a counterion:
—COO$^-$, —SO$_3^-$, —OSO$_3^-$, —PO$_3^{2-}$, —OPO$_3^{2-}$,
—(OCH$_2$CH$_2$)$_s$—O—(CH$_2$)$_t$—COO$^-$,
—(OCH$_2$CH$_2$)$_s$—O—(CH$_2$)$_t$—SO$_3^-$,
—(OCH$_2$CH$_2$)$_s$—O—(CH$_2$)$_t$—OSO$_3^-$,
—(OCH$_2$CH$_2$)$_s$—O—(CH$_2$)$_t$—PO$_3^{2-}$, or
—(OCH$_2$CH$_2$)$_s$—O—(CH$_2$)$_t$-OPO$_3^{2-}$;
or of the following formulae A, B or C,

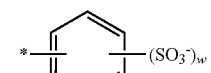

A

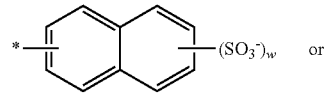

B

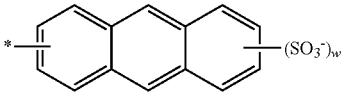

C wherein * marks the point of attachment of the X group, s is an integer of 1 to 1,000, t is an integer of 1, 2, 3 or 4 and w is an integer of 1, 2 or 3;

wherein the cationic groups are:
—NR¹R²R³⁺Z⁻, —PR¹R²R³⁺Z⁻, or one of the following formulae:

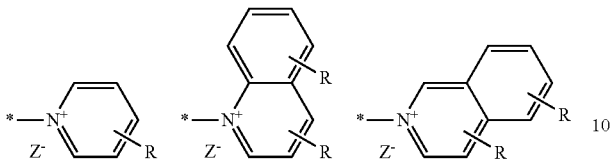

wherein * marks the point of attachment of the X group, $R^1$, $R^2$ and $R^3$ each, independently of one another, are H, $C_{1-30}$-alkyl, Ar or —CH₂Ar wherein Ar is an unsubstituted or mono- or polysubstituted aromatic ring or condensed ring system having 6 to 18 C atoms, wherein one or two CH groups may be replaced by N, R is H or $C_{1-4}$-alkyl in any ring position, and $Z^-$ is $Cl^-$, $Br^-$, $I^-$, $CH_3SO_3^-$, $CF_3SO_3^-$, $CH_3PhSO_3^-$, or $PhSO_3^-$;

wherein the nonionic groups are:
linear or branched alkyl, wherein one or more non-adjacent C atoms have been replaced by O, S, and/or N;
—OH, —SH, —O-(glycoside)$_{o'}$, —S-(glycoside)$_{o'}$, —OCH₂—CHOH—CH₂—O H, —OCH₂Ar(—NCO)$_{p'}$, —OAr(—NCO)$_{p'}$, or amine oxide, wherein o' is an integer of 1 to 10, p' is 1 or 2, Ar is an unsubstituted, mono- or polysubstituted aromatic ring or condensed ring system having 6 to 18 C atoms, wherein one or two CH groups may be replaced by C═O and glycoside is an etherified carbohydrate;
one of the following formulae

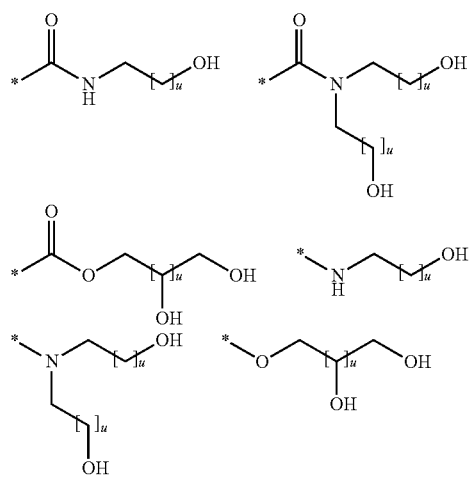

wherein * marks the point of attachment of the X group, and u is an integer of 1 to 6;
or the group $R^4$—(O—CH₂CHR⁵)$_{m'}$— wherein m" is an integer of 1 to 100 and $R^4$ and $R^5$ are H or $C_{1-4}$-alkyl;
or —CH(OH)—CH₂—NH-Sach wherein Sach is a sugar;
or —Y—(CH₂—CH₂—O)$_v$—R⁴ wherein Y═S, O or NH, $R^4$═H or alkyl, and v=1-100; and wherein the amphoteric groups are:
functional groups of the acetyldiamines, the N-alkylamino acids, the N-alkylaminosulfonic acids, the betaines or the sulfobetaines;
a group of one of the following formulae:

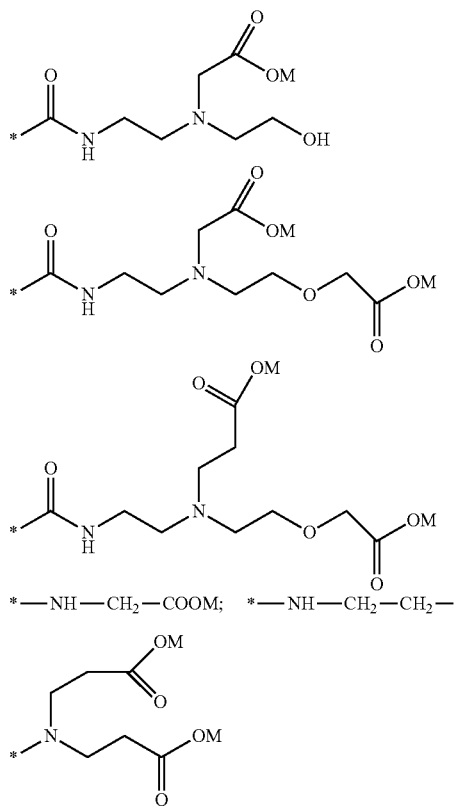

wherein * marks the point of attachment of the X group and M is H or an alkali-metal ion;

—[(C(═O)—NH—(CH₂)$_{(1-8)}$]$_{(0 or 1)}$—N⁺R¹R²—CH₂—COO⁻, wherein $R^1$ and $R^2$ each, independently of one another, a $C_{1-8}$-alkyl radical, or —(C(═O)—NH—(CH₂)$_{1-3}$—N⁺R¹R²—CH₂—CH(OH)—CH₂—(O)$_{(0 or 1)}$—(S or P)O₃⁻, wherein $R^1$ and $R^2$ each, independently of one another, a $C_{1-8}$-alkyl radical.

15. A method comprising adding a compound according to claim 1 as an additive to a composition selected from the group consisting of: paints, coatings, printing inks, protective coatings, special coatings in electronic or optical applications, photoresists, top antireflective coatings, bottom antireflective coatings, developer solutions and wash solutions and photoresists for photolithographic processes, cosmetic products, agrochemicals, floor polishes, photographic coatings and coatings of optical elements.

16. Composition comprising a compound according to claim 1 and a vehicle which is suitable for application in a: paint or coating preparation, fire-extinguishing composition, lubricant, washing or cleaning composition, de-icer, developer solution, rinse solution, immersion oil, photoresist for a photolithographic process, agrochemical, floor polish, cosmetic product, hydrophobicising composition for textile finishing or glass treatment or printing ink; and optionally further specific active substances.

17. Composition according to claim 16, characterised in that the composition is selected from the group consisting of: paint and coating preparations, fire-extinguishing compositions, lubricants, washing and cleaning compositions, de-icers, developer solutions and wash solutions and photoresists for photolithographic processes, cosmetic products, agrochemicals, floor polishes and hydrophobicising compositions for textile finishing or glass treatment.

* * * * *